United States Patent [19]
Fleet

[11] 4,059,406
[45] Nov. 22, 1977

[54] ELECTROCHEMICAL DETECTOR SYSTEM

[75] Inventor: Bernard Fleet, London, England

[73] Assignee: E D T Supplies Limited, London, England

[21] Appl. No.: 704,299

[22] Filed: July 12, 1976

[51] Int. Cl.² ............... G01N 27/26; G01N 27/30; G01N 31/08

[52] U.S. Cl. .............. 23/230 R; 23/253 R; 73/61.1 C; 204/1 T; 204/195 R

[58] Field of Search ......... 23/230 R, 253 R, 232 E, 23/254 E; 73/23.1, 61.1 C; 204/195 R

[56] References Cited

U.S. PATENT DOCUMENTS

| | | | |
|---|---|---|---|
| 3,352,643 | 11/1967 | Ando et al. | 23/253 X |
| 3,535,084 | 10/1970 | Izawa et al. | 23/232 E |
| 3,902,848 | 9/1975 | Juvet, Jr. et al. | 23/253 R |

*Primary Examiner*—R.E. Serwin
*Attorney, Agent, or Firm*—Behr & Woodbridge

[57] ABSTRACT

An electrochemical detector has an electrochemical thin-layer flow cell whose operation is based on the so-called wall-jet principle, in combination with a controller unit. The controller unit can apply a periodically changing voltage having a square wave voltage formation to a sensor electrode of the electrochemical cell such that a first potential level of the square wave functions as a detecting potential and a second potential level of the square wave functions as a cleaning potential.

18 Claims, 6 Drawing Figures

| Oxidation Mode | | Reduction Mode |
|---|---|---|
| ← → hydrocarbons | olefins | ← → |
| ← → azines/triazines | esters | ← → |
| ← → amino acids | ketones | ← → |
| ← → amines/amides | aldehydes | ← → |
| ← → phenothiazines | olfinic esters | ← → |
| ← → phenols | ethers | ← → |
| ← → aromatic OH | organometallics | ← → |
| ← → quinolines | diazo c'p'ds | ← → |
| ← → imines | nitro c'p'ds | ← → |
| ← → | halogens | ← → |
| +2  +1  0 | | 0  −1  −2 |
| (volts vs. S.C.E.) | | (volts vs. S.C.E.) |

Electroactivity of a range of organic functional groups.

*Fig. 6*

ELECTROCHEMICAL DETECTOR SYSTEM

FIELD OF THE INVENTION

The present invention relates to an electrochemical detector and to a method for detecting one or more electroactive species.

BACKGROUND OF THE INVENTION

In the past electrochemical detector techniques have been widely used for on-line voltammetry and low resolution liquid chromatography. However despite the rapid advances that have been made in the column technology of high pressure liquid chromatography, a serious limitation to development and use of this method has been the lack of a suitable detector system. High pressure liquid chromatography involves the resolution of substances which are only present in the eluting solution in trace amounts. The requirements of an electrochemical technique to detect such trace eluents are (1) high sensitivity (2) detectors with ultra-low cell volume (3) a wide range of response (4) large linear range of operation (5) little influence of experimental parameters, e.g. temperature, flow rate etc. and (6) long term stability and reliability.

SUMMARY OF THE INVENTION

The present invention provides an electrochemical cell and controller unit which fulfill most of the above requirements and in addition overcome many of the conventional problems encountered in on-line voltammetry.

According to the present invention we provide an electrochemical detector having an electrochemical thin-layer flow cell adapted to operate on the wall-jet principle and comprising a sensor electrode, a solution inlet line terminating in a fine nozzle, the said nozzle being located normally to but displaced from a surface of the sensor electrode, at least one solution exit line, at least one other electrode and means comprising a controller unit for applying a periodically changing voltage to the sensor electrode so that a first part of each cycle of the applied voltage functions as a detecting potential and second part of each cycle of the applied voltage functions as a cleaning potential.

According to the invention we also provide a method for detecting one or more electroactive species in a flow stream by means of the said electrochemical detector.

In a preferred embodiment of the invention an inlet solution impinges as a jet normally at the centre of a planar surface of a disc-shaped sensor electrode, the electrode consisting of high density vitreous carbon.

The cell design of the present invention is based on the socalled wall-jet principle which gives very high efficiency in terms of mass transfer to the electrode irrespective of cell volume and thus allows detection of substances down to the sub-nanogram ($10^{-9}$g) range. The application of the wall-jet principle to an electrochemical flow cell was first disclosed by Yamada J. and Matsuda H. in J. Electroanal. Chem. 44 189 (1973). A wall-jet electrode in-line with a high pressure liquid chromatography column was first disclosed by the present inventor and another in J. Chromat. Sci. 12 747 (1974). Although such an arrangement was used successfully to detect electroactive species only present in the column effluent in trace amounts, the electrochemical cell had to be frequently dismantled in order to clean the sensor electrode surface by mechanical means e.g. polishing. Products of electrolysis tend to accumulate at the sensor electrode surface which, unless removed, unfavourably affect the working of the sensor electrode and the accuracy of the results obtained. The present invention provides a means for continuously removing products of electrolysis from the sensor electrode surface thus maintaining a clean working surface for long periods of time. A periodically changing voltage is applied to the sensor electrode so that a first part of the applied voltage functions as a detecting potential and a second part of the applied voltage functions as a cleaning potential. A stable, reliable and continuously operable electrochemical detector suitable for commercial application is thus provided.

In a preferred embodiment of the invention a reference electrode and a tubular counter electrode are located radially to the disc electrode, the tubular counter electrode being contained in a solution exit line.

DESCRIPTION OF THE DRAWINGS

A particular embodiment of the invention and method by which it is to be performed will now be described with reference to the accompanying drawings wherein:

FIG. 6 is a table illustrating the electroactivity of a range of organic functional groups which can be detected by the electrochemical detector of the present invention.

DESCRIPTION OF PREFERRED EMBODIMENTS

Figure 1:
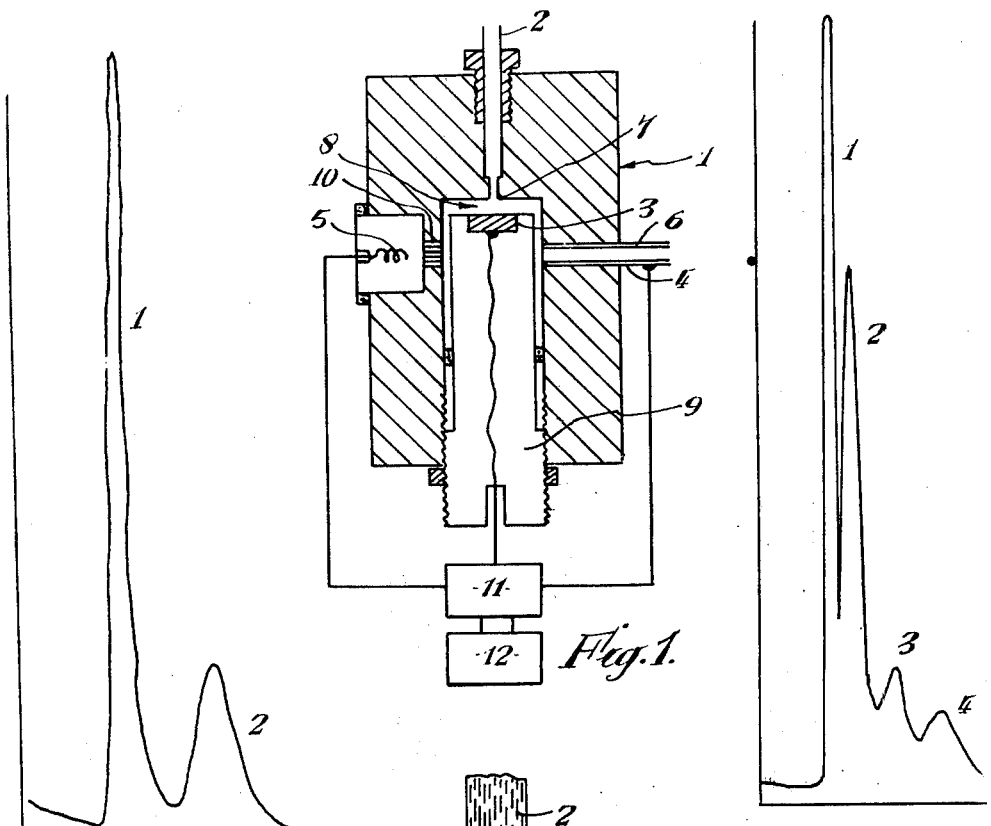
FIG. 1 is a schematic diagram of the invention.

As shown in FIG. 1 an electrochemical flow cell 1 has an inlet line 2, a sensor electrode 3, an exit line 4, a tubular counter electrode 5 and a reference electrode 6. The inlet line 2 terminates in a fine nozzle and is located normally to the centre of a planar surface of the disc sensor electrode 3. The distance between the fine nozzle and the sensor electrode surface forms the axial limit of a cylindrical space 8 which includes an "effective cell volume". The sensor electrode 3 is held in position by means of a screw mount 9. The cylindrical space 8 and hence the effective cell volume can thus be varied by fine adjustment of the screw mount 9. With a disc sensor electrode 3 mm in diameter the "effective cell volume" could be varied from less than 1 $\mu$l to 100 $\mu$l ($10^{-6}$l). In place of a disc-shaped sensor electrode a ring or a split-ring electrode 3, as indicated by dotted lines in FIG. 2, may be employed.

The tubular counter electrode 5 and the reference electrode 6 are located radially to the disc electrode 3 and diametrically opposed to each other. The reference electrode 6 contacts the solution through a porous junction 10 and the tubular counter electrode 5 is located in exit line 4, both of which are necessarily downstream of the sensor electrode 3. An alternative to the electrode mode shown in FIG. 1 is a two electrode mode consisting of a sensor electrode and reference electrode only. The provision and mode of use of reference and counter electrodes is per se known. In an alternative embodiment of the invention the reference electrode 6 is contained in a second solution exit line either with or without a counter electrode present. In any of these electrode modes the potential across the cell is controlled and monitored by a controller unit 11 which is connected to a recorder unit e.g. a pen recorder 12.

The sensor electrode 3 is preferably made of high density vitreous carbon due to its wide operating potential range, typically from $+1.3V$ to $-1.0V$ vs. calomel reference electrode, and its relative freedom from surface film effects.

Conventional electrode materials such as platinum, gold or impregnated graphite may alternatively be employed.

The operation of the electrochemical cell 1 and controller unit 11 will now be described.

Figures 2, 4, 5:
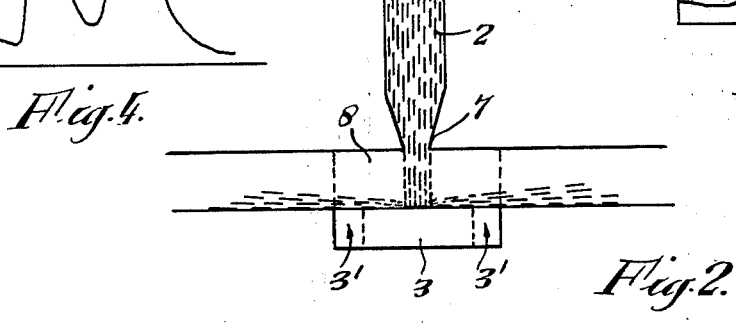
FIG. 2 is a detail from FIG. 1 to show the working of a wall-jet electrode.
FIGS. 4 and 5 are chart recordings with respect to examples 1 and 2 respectively.

The solution, for example the effluent from a high performance, high pressure liquid chromatography column, enters the cell 1 through the inlet line 2 and is forced by that pressure through the fine nozzle 7 to form a jet of solution. This jet impinges at the centre of the disc sensor electrode 3 and spreads radially over the surface of the electrode in a thin film as shown in FIG. 2.

An electrochemical cell, operating on the wall-jet principle as just described, includes an "effective cell volume" and a "dead cell volume". The "effective cell volume" is contained in the cylindical space 8 as stated above, whilst any solution downstream of the sensor electrode is contained in the "dead cell volume" and has no effect on the sensitivity of the cell. After flowing over the sensor electrode surface the solution passes into the cylindrical cell volume where it makes contact with the reference electrode 6 via the porous junction 10 and then leaves the cell via the tubular counter electrode 5.

To control and monitor the potential across the cell 1 the controller unit 11 applies a periodically changing voltage to the sensor electrode 3 such that a first part of the applied voltage functions as a detecting potential and a second part of the applied voltage functions as a cleaning potential. Any products of electrolysis which have accumulated at the sensor electrode surface during a detecting step are thus re-oxidised or re-reduced during a cleaning step and the sensor electrode surface area is maintained at a substantially constant value. The voltage is applied either in the conventional potentiostatic configuration employing the three electrode system in which the reference electrode 6 is used to monitor and control the potential of the sensor electrode 3, or in the standard two electrode system. In either system the amplitude and polarity of the detecting potential may be varied. The sensor electrode 3 may therefore operate as a cathode for the detection of electroreducible species or as an anode for the detection of electrooxidisable species.

Figure 3:
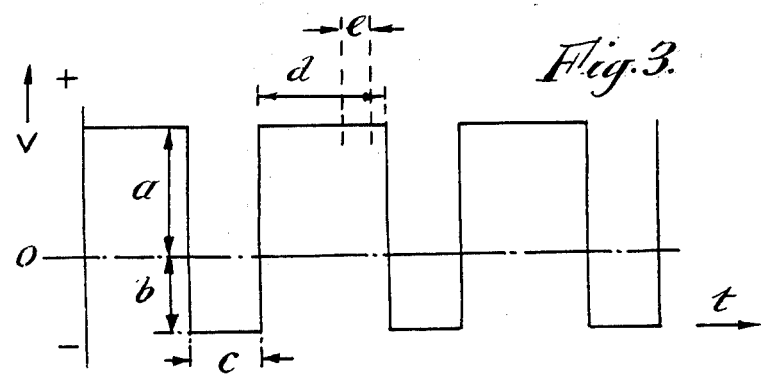
FIG. 3 is a diagrammatic representation of a square wave voltage potential.

The controller unit includes a switching circuit so that the periodically changing voltage applied to the sensor electrode may have a square wave voltage formation which may be regarded as a periodic voltage, which may be varied in amplitude, added to a variable d.c. voltage reference level. An example of such a square wave is shown in FIG. 3 in which voltage V is measured along the ordinate and time $t$ along the abscissa. The amplitude (a) and (b) of each polarity of the square wave may be independently varied according to the electroactive species under investigation and what other species are present. In FIG. 3 if the electroactive species is electro-oxidisable then (a) is the detecting potential and (b) is the cleaning potential. The polarity of the cleaning potential is selected so as to ensure that any products of electrolysis which may have accumulated at the electrode during the detecting potential, for example by electro adsorption, are (in this example) rereduced and desorbed from the surface. The electrode surface is thus cleaned and ready for the next detecting step. Alternatively, depending on the species under investigation, sufficient desorption from the electrode surface may occur if the cleaning potential is equal to zero or even of the same polarity as the detecting potential provided that (b) does not exceed (a).

Similarly, in FIG. 3 time components (c) and (d) of each potential level of the square wave may be independently altered in order to achieve the optimum working conditions for the species under investigation. The current is only measured for a short period, for example the period (e) corresponding to the time required for one cycle of the local mains voltage supply, (usually 50 Hz or 60Hz), towards the end of the detecting potential level. The principal of this measuring technique is well established and arises from the need to discriminate the faradaic current due to reduction or oxidation of the measured species from the capacitative double layer charging current which is intially large but decays rapidly.

Typical applications for which the electrochemical detector is suitable are the continuous monitoring of trace electroactive materials in water, continuous flow anodic stripping voltammetry and organic electroanalytical chemistry. Examples of electroactive materials which can be detected by the present invention include heavy metals such as mercury, lead, copper and cadmium, as well as electroactive organic species such as phenols. In continuous flow anodic stripping voltammetry a small amount of mercuric ions is added to the inlet solution and the metal ion $i$ of interest is simultaneously deposited as an amalgam in a thin mercury film on the surface of the carbon electrode. During the subsequent electrolytic dissolution of the film the anodic current is used to measure the initial concentration of the metal ion $i$ in the solution.

FIG. 6 is a table illustrating the electroactivity of a range of organic functional groups which can be detected by the electrochemical detector of the present invention. The following examples are illustrative of its application in combination with a high performance, high pressure liquid chromatography column having duct means for an effluent from the column to enter the solution inlet line of the electrochemical cell.

EXAMPLE 1

5 $\mu$l of a solution containing $10^{-2}$ g/l of (1) methyl-4-hydroxybenzoate in 20% MeOH/Water V/V (containing 0.1M $KNO_3$) and 5 $\mu$l of a solution containing $10^{-2}$ g/l of (2) n-propylhydroxybenzoate in 20% MeOH/Water V/V (containing 0.1M $KNO_3$) were injected into the head of a 50 cm ODS "Permaphase" (Registered Trade Mark) column and eluted at a flow rate of 1.2 ml/min. The effluent from the column was fed into the inlet line of the electrochemical cell and a square wave voltage at a frequency of 5 Hz was applied to a high density vitreous carbon sensor electrode. Using a detecting potential of $+1.2$ V vs. Ag/AgCl for 160 ms of each cycle and a cleaning potential of $-0.2$ V for the remaining 40 ms of each cycle, both compounds (1) and (2) were detected. A distinct peak was recorded by the pen recorder for each compound as shown in a chart recording illustrated in FIG. 4 in which current is measured along the ordinate and time along the abscissa.

EXAMPLE 2

5 μl solutions of each of (1) 4-methoxy-phenol, (2) 4-aminophenol, (3) 4-nitrophenol and (4) 4-chlorophenol each in MeOH/Water 5% V/V (containing 0.1 MKNO$_3$) at a concentration of $10^{-2}$g/l were injected into the head of a 50 cm ODS "Permaphase" (Registered Trade Mark) column and eluted at a flow rate of 1.0 ml/min. The effluent from the column was fed into the inlet line of the electrochemical cell and a square wave voltage at a frequency of 5Hz was applied to a high density vitreous carbon sensor electrode.

Using a detecting potential of +1.1 V vs. Ag/AgCl for 160 ms of each cycle and a cleaning potential of −0.2 V for the remaining 40 ms of each cycle, each of the phenol derivatives (1,2,3 and 4) were detected. A chart recording, having current measured along the ordinate, and time along the abscissa, made by the pen recorder for the present example is illustrated in FIG. 5.

I claim:

1. A method for detecting an electroactive species in a flow stream comprising the steps of:
   i. forcing a solution containing the electroactive species through a fine nozzle to form a jet,
   ii. impringing the jet normally to a surface of a sensor electrode so that the solution spreads radially over the surface in a thin film,
   iii. applying a periodically changing voltage to the sensor electrode, so that one part of each cycle of the applied voltage functions as a detecting potential and another part of each cycle functions as a cleaning potential, and
   iv. measuring a current at the sensor electrode during that part of each cycle of the applied voltage functioning as a detecting potential.

2. A method for detecting an electroactive species as claimed in claim 1 comprising the further step of:
   v. recording the current measured at the sensor electrode.

3. A method for detecting an electroactive species as claimed in claim 1 which consists of applying a square wave voltage to the sensor electrode, a first level of each cycle of the applied square wave functioning as a detecting potential and a second level of each cycle functioning as a cleaning potential.

4. In an electrochemical detector having an electrochemical thin-layer flow cell adapted to operate on the wall-jet principle comprising a solution inlet line terminating in a fine nozzle, a sensor electrode, at least one solution exit line, and at least one other electrode, the improvement comprising means for applying a periodically changing voltage to the sensor electrode so that a first part of each cycle of the applied voltage functions as a detecting potential and a second part of each cycle of the applied voltage functions as a cleaning potential.

5. The improvement claimed in claim 4 wherein the periodically changing voltage applied to the sensor electrode is a square wave voltage.

6. The improvement claimed in claim 5 wherein a first level of each square wave cycle functions as a detecting potential and a second level of each square wave cycle functions as a cleaning potential.

7. The improvement claimed in claim 6 wherein a current is measured for a short period towards the end of each level which functions as a detecting potential.

8. The improvement claimed in claim 7 wherein the short period is equal to the time required for one cycle of mains voltage.

9. The improvement claimed in claim 5 comprising means for altering the amplitude of the square wave voltage.

10. The improvement claimed in claim 6 comprising means for altering the frequency of the square wave voltage and the length of the said first and second level independently of each other.

11. An electrochemical detector having an electrochemical thin-layer flow cell adapted to operate on the wall-jet principle comprising a sensor electrode, a solution inlet line terminating in a fine nozzle, the said nozzle being located normally to but displaced from a surface of the sensor electrode, at least one solution exit line, at least one other electrode and means comprising a controller unit for applying a periodically changing voltage to the sensor electrode so that one part of each cycle of the applied voltage functions as a detecting potential and another part of each cycle of the applied voltage functions as a cleaning potential.

12. An electrochemical detector as claimed in claim 11 comprising means for altering the distance between the fine nozzle and the surface of the sensor electrode.

13. An electrochemical detector as claimed in claim 11 wherein the said electrochemical cell has an effective cell volume in the range from less than 1 μl ($10^{-6}$l) to 100 μl ($10^{-6}$l).

14. An electrochemical detector as claimed in claim 11 wherein the sensor electrode surface is planar and the sensor electrode is disc-shaped.

15. An electrochemical detector as claimed in claim 11 wherein the sensor electrode is in ring form.

16. An electrochemical detector as claimed in claim 11 wherein the sensor electrode consists of high density vitreous carbon.

17. An electrochemical detector as claimed in claim 11 wherein the electrochemical thin-layer flow cell has one solution exit line, a reference electrode and a counter electrode.

18. An electrochemical detector as claimed in claim 11 in combination with a high performance, high pressure liquid chromatography column having duct means for an effluent from the said column to enter the solution inlet line of the said electrochemical cell.

* * * * *